(12) United States Patent
Vild et al.

(10) Patent No.: US 10,267,750 B2
(45) Date of Patent: Apr. 23, 2019

(54) SYSTEM AND ASSOCIATED METHOD FOR ONLINE DETECTION OF SMALL DEFECTS ON/IN A GLASS SHEET

(71) Applicant: Glasstech, Inc., Perrysburg, OH (US)

(72) Inventors: Michael J. Vild, Toledo, OH (US); Benjamin L. Moran, Perrysburg, OH (US); Jason C. Addington, Sylvania, OH (US)

(73) Assignee: Glasstech, Inc., Perrysburg, OH (US)

( * ) Notice: Subject to any disclaimer, the term of this patent is extended or adjusted under 35 U.S.C. 154(b) by 46 days.

(21) Appl. No.: 15/428,401

(22) Filed: Feb. 9, 2017

(65) Prior Publication Data

US 2018/0224381 A1   Aug. 9, 2018

(51) Int. Cl.
*G06K 9/46* (2006.01)
*G06K 9/48* (2006.01)
(Continued)

(52) U.S. Cl.
CPC ....... *G01N 21/958* (2013.01); *G01N 21/8806* (2013.01); *G01N 21/8851* (2013.01); *G06K 9/4604* (2013.01); *G06T 7/0004* (2013.01); *C03B 23/023* (2013.01); *C03B 29/08* (2013.01); *C03B 35/205* (2013.01);
(Continued)

(58) Field of Classification Search
CPC .................................................. G01N 21/958
See application file for complete search history.

(56) References Cited

U.S. PATENT DOCUMENTS

| 4,149,784 A | * | 4/1979 | Johnson | G03B 21/11 353/121 |
| 5,558,927 A | * | 9/1996 | Aruga | G02B 5/201 359/589 |

(Continued)

FOREIGN PATENT DOCUMENTS

WO   20160140753 A1   9/2016

OTHER PUBLICATIONS

World Intellectual Property Organization, International Search Report and Written Opinion of corresponding International Application No. PCT/US2018/017397, dated Apr. 26, 2018.
(Continued)

*Primary Examiner* — Tracy Y. Li
(74) *Attorney, Agent, or Firm* — Brooks Kushman P.C.

(57) ABSTRACT

A small defect detection apparatus installed online in a glass sheet processing system includes a line scan camera, a background screen including contrasting elements arranged in a pre-defined pattern, an upstream conveyor and a downstream conveyor, wherein the upstream conveyor and downstream conveyor are positioned end-to-end, spaced apart by a selected size gap such that the camera may acquire multiple images of the background screen as the unsupported portion of the glass sheet is conveyed over the gap, and a computer programmed to execute logic for receiving the set of image data comprising multiple images of the background screen and identifying small defects in the glass from the data. The system may also include a glass sheet part identifier and a programmable control including logic for analyzing acquired image data and selecting an area of interest on the glass sheet for the analysis.

10 Claims, 6 Drawing Sheets

(51) Int. Cl.
  *G06T 7/00* (2017.01)
  *C03B 29/08* (2006.01)
  *C03B 35/20* (2006.01)
  *G01N 21/88* (2006.01)
  *C03B 23/023* (2006.01)
  *G01N 21/958* (2006.01)

(52) U.S. Cl.
  CPC ............... *G01N 2021/8832* (2013.01); *G01N 2021/8887* (2013.01); *G06K 9/482* (2013.01); *G06T 2207/30108* (2013.01)

(56) References Cited

U.S. PATENT DOCUMENTS

| | | | |
|---|---|---|---|
| 6,437,357 B1 | 8/2002 | Weiss et al. | |
| 6,705,526 B1* | 3/2004 | Zhu | B82Y 15/00 235/462.01 |
| 7,386,161 B2 | 6/2008 | Weiss et al. | |
| 2004/0057046 A1* | 3/2004 | Abbott | G01B 11/306 356/239.1 |
| 2006/0108346 A1 | 5/2006 | Janhunen | |
| 2009/0081930 A1* | 3/2009 | Vianello | B24B 9/102 451/44 |
| 2010/0096069 A1* | 4/2010 | Vianello | E06B 3/66352 156/101 |
| 2012/0098959 A1 | 4/2012 | Addington | |
| 2012/0099167 A1* | 4/2012 | Ciardullo | H04N 1/00588 358/498 |
| 2013/0123985 A1 | 5/2013 | Hirai et al. | |
| 2013/0211736 A1 | 8/2013 | Hess et al. | |
| 2014/0270391 A1 | 9/2014 | Addington | |
| 2015/0308943 A1* | 10/2015 | Vild | G01N 21/896 356/239.1 |
| 2016/0225036 A1 | 8/2016 | Nguyen | |
| 2016/0257598 A1 | 9/2016 | Vild et al. | |
| 2017/0302902 A1 | 10/2017 | Martinello et al. | |

OTHER PUBLICATIONS

World Intellectual Property Organization, International Search Report and Written Opinion of International Application No. PCT/US2018/017388, dated Apr. 19, 2018.

* cited by examiner

SYSTEM AND ASSOCIATED METHOD FOR ONLINE DETECTION OF SMALL DEFECTS ON/IN A GLASS SHEET

TECHNICAL FIELD

This invention relates to a method and apparatus for measuring small defects in glass sheets installed in-line in a glass sheet processing system.

BACKGROUND

Manufacturers of glass sheets, particularly glass sheets formed into various curved shapes for use as automotive windshields, backlites, and sidelites, desire to identify small marks or other defects that are visible on the surface of or within the formed sheets that might be perceived by a human observer, such as the operator or passenger in a vehicle in which the glass may be mounted as the windshield, backlite, or sidelite.

Various types of glass sheet optical inspection systems are known. One known optical inspection system is disclosed in United States Application Publication No. 2012/0098959 A1, which application is also assigned to the assignee of the invention disclosed herein. This disclosed optical inspection system may be implemented in either a laboratory (i.e., off-line) or an in-line configuration in which the inspection system is mounted to inspect glass sheets to measure and evaluate the amount of transmitted optical distortion, as well as to detect and measure small defects in the formed sheets as they are being conveyed in a processing system, such as, for example, is disclosed in United States Application Publication No. 2016/0257598 A1, which application is also assigned to the assignee of the invention disclosed herein. This disclosed system includes a glass sheet acquisition and positioning mechanism to remove the glass sheet, and retain and accurately position the sheet in a preselected position, such as, for example, the installation angle of the glass sheet in a vehicle, to more accurately measure the transmitted distortion that might be perceived by a vehicle occupant.

In these and other known systems, however, the data from a single camera, acquired at a single preselected position, is utilized for both the transmitted optical distortion and the small defects analyses. While this approach minimizes the amount and frequency of image data acquisition, the optimal image acquisition parameters (e.g., image resolution, position of glass sheet relative to the background screen, background screen pattern) differ for these two analyses.

It may be useful to utilize a method and apparatus that is optimized for, and dedicated solely to, detecting and measuring small defects in glass sheets.

SUMMARY

The disclosed apparatus and associated method for detecting and measuring small optical or obstructive defects in a selected area of the glass sheet includes a background screen including contrasting elements arranged in a pre-defined pattern, a camera for acquiring a set of image data comprising at least one image of the background screen associated with the selected area of the glass sheet as the glass sheet moves to a preselected position on the conveyor between the camera and the background screen, and a computer including at least one processor programmed to execute logic for receiving the image data, developing an intensity map from the image data set, and identifying and locating the small defects from the intensity map.

In one disclosed embodiment, the camera is a line scan camera, the background screen extends across the full dimension of the selected area in the direction transverse to the direction of conveyance, and the set of image data comprises data from multiple line scan images of the glass sheet as the glass sheet is conveyed across the path between the camera and the background screen.

In one disclosed embodiment, the apparatus includes an upstream conveyor and a downstream conveyor, each of which convey each glass sheet in a generally horizontal orientation. The upstream conveyor and downstream conveyor are positioned end-to-end with their adjacent ends spaced apart by a selected size gap such that, as a glass sheet is conveyed from the upstream conveyor to the downstream conveyor, a portion of the glass sheet is unsupported over the gap. In this disclosed embodiment, the background screen is mounted such that the camera may acquire multiple images of the background screen as the unsupported portion of the glass sheet is conveyed between the adjacent upstream and downstream conveyors.

The disclosed apparatus may also include a glass sheet part identifier including a sensor mounted at a desired location upstream from the glass sheet support frame for acquiring data associated with the shape of the glass sheet. The programmable control may also include logic for analyzing the acquired data and identifying the glass sheet as one of a set of know part shapes, and/or selecting a desired area on the glass part for conducting the small defect analysis. In one embodiment, the sensor is the camera and the data associated with the shape of the glass sheet is developed from the set of image data acquired by the camera for use in detecting/measuring small optical or obstructive defects.

In one disclosed embodiment, the disclosed apparatus and method for measuring small defects in glass sheets is installed in-line in a system for fabricating glass sheets including a heating station for heating the glass sheet to a temperature adequate to soften the glass for forming into a desired shape, a bending station wherein the softened sheet is formed to the desired shape, a cooling station wherein the formed glass sheet is cooled in a controlled manner.

The disclosed apparatus also includes at least one computer including the previously described part-shape identification logic, as well as logic for receiving the captured image data sets and performing the above-described optical processing operations to analyze the optical characteristics of the glass sheet and display or otherwise report selected information associated with the analyses.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
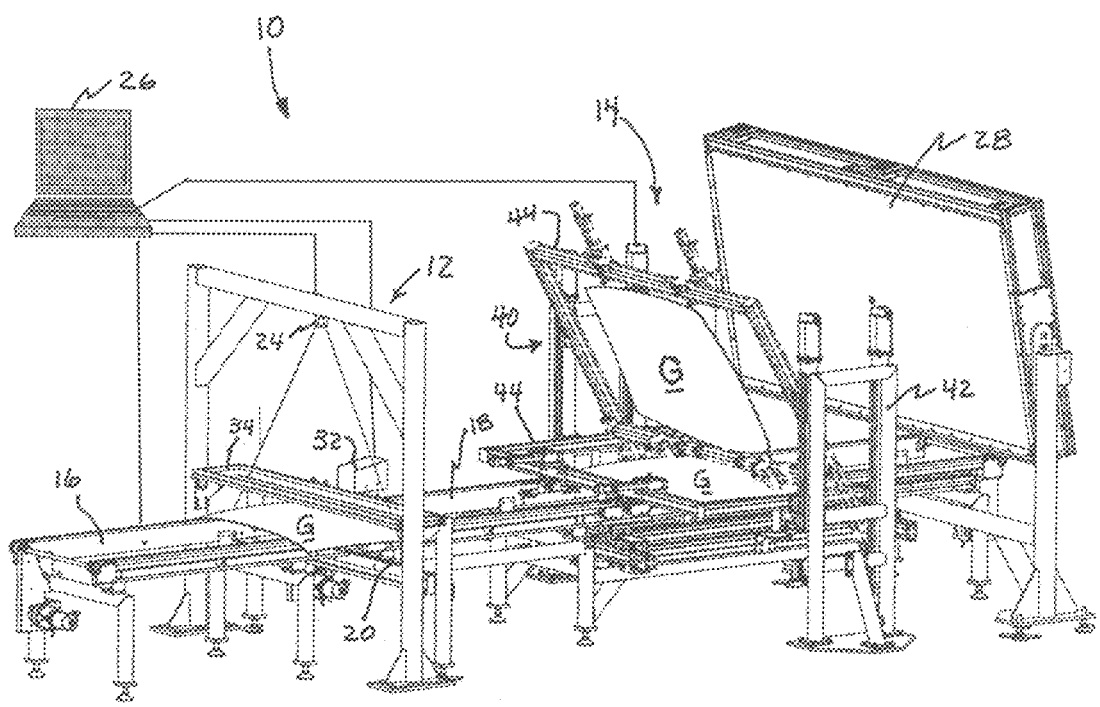
FIG. 1 is a perspective view of one embodiment of the disclosed glass sheet optical inspection system.
Figure 2:
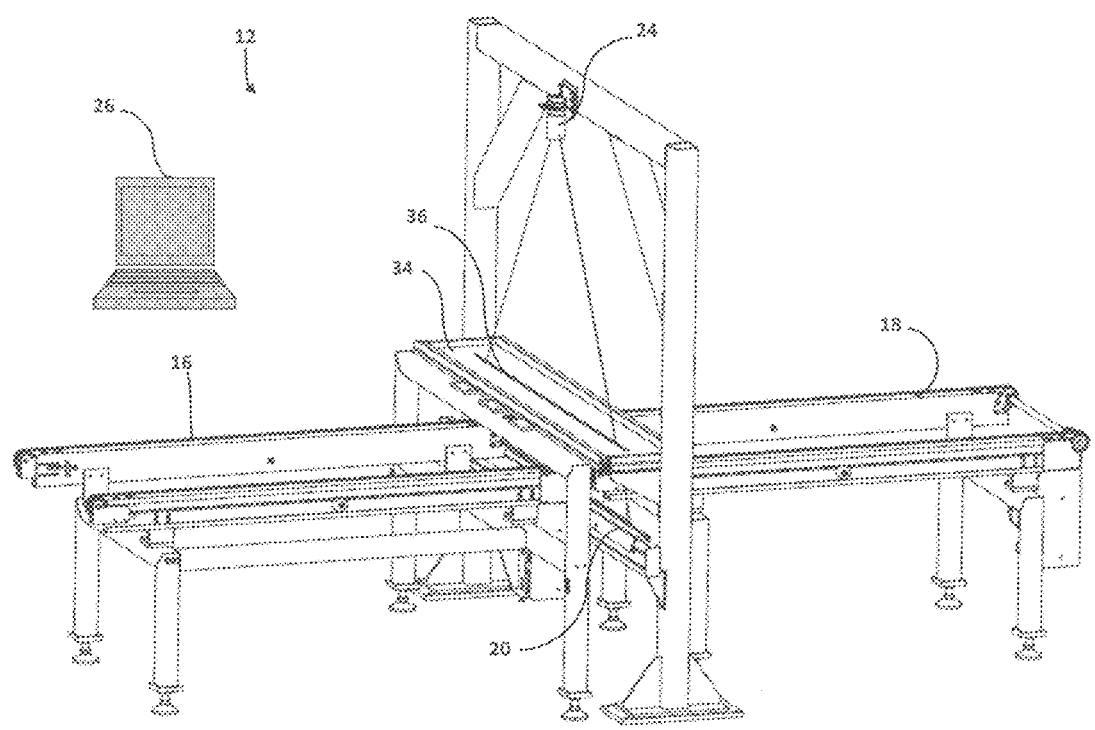
FIG. 2 is a perspective view of one embodiment of the apparatus for measuring small optical or obstructive defects which may be employed in the system of FIG. 1.

Referring to FIG. 1, an online glass sheet optical characteristics inspection system generally indicated as 10, includes an apparatus for identifying and measuring small defects 12 and an apparatus for measuring transmitted optical distortion 14. The system 10 may be installed in a system for fabricating glass sheets including one or more processing stations and one or more conveyors 16, 18 for conveying the glass sheet from station to station during processing.

Figures 3, 4, 5:
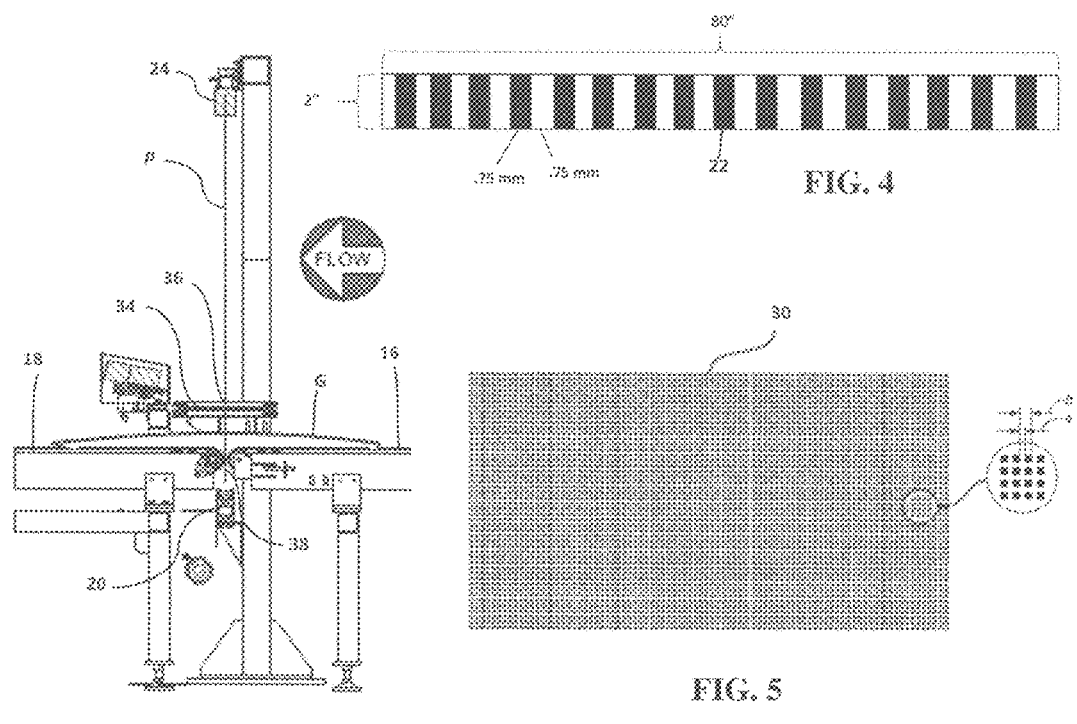
FIG. 3 is a partial side view of the adjacent ends of the upstream and downstream conveyors and a first background screen which may be utilized in the apparatus of FIG. 2.
FIG. 4 is one embodiment of a first background screen pattern which may be utilized in the apparatus for measuring small optical or obstructive defects.
FIG. 5 is one embodiment of a first background screen pattern which may be utilized in the apparatus for measuring transmitted optical distortion.

The apparatus for identifying and measuring small defects 12 may include a first background screen 20 including contrasting elements arranged in a predefined pattern 22 (such as is shown in FIG. 4), a first camera 24 for acquiring a first set of image data comprising at least one image of the first background screen 20 associated with a first selected area of a glass sheet G as the glass sheet G moves to a preselected position on the conveyor between the camera and the first background screen. The first selected area may be any pre-defined area on the surface of the glass sheet within which the small defects identification is desired. In the disclosed embodiment, the small defects apparatus 12 may allow for the first selected area to be the entire surface of a glass sheet.

The small defects apparatus 12 may also include at least one computer and/or programmable control (generally indicated as 26) which includes at least one processor program to execute logic for controlling the first camera to acquire the desired number and frequency of images for each glass sheet, receiving the first set of image data from the images, and analyzing the first set of image data to identify small defects located within the first selected area.

Figure 6:
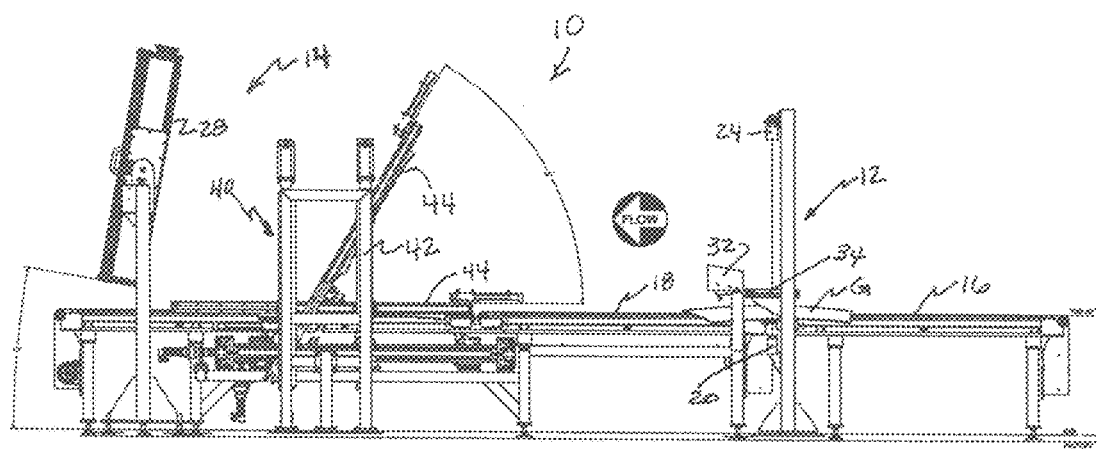
FIG. 6 is a side view of one embodiment of the disclosed glass sheet optical inspection system.

Referring still to FIG. 1, the apparatus for measuring transmitted optical distortion 14 may include a second background screen 28 including contrasting elements arranged in a predefined pattern 30 (such as is shown in FIG. 5), a second camera 32 for acquiring an image of the second background screen 28 with a glass sheet positioned between the second camera 32 and the screen 28 at a preselected position (such as is shown in FIG. 6), and one or more computers and/or programmable controls 26 including logic for controlling the second camera 32 and processing the acquired data to analyze the optical distortion characteristics of the glass sheet.

It should be appreciated that the small defects apparatus 12 and the optical distortion apparatus 14 may each, alternatively, be implemented as stand-alone systems if desired rather than the integrated small defects/transmitted optical distortion online system shown in FIGS. 1 and 6. It should also be appreciated that each of the small defects and transmitted optical distortion measurement capabilities may be optimized by utilizing separate cameras and background screens for each of the small defects apparatus 12 and the optical distortion apparatus 14 in the disclosed integrated system 10, since, for example, image resolution, camera angle, and background pattern may be optimized separately for each of the small defects and optical distortion systems/functions.

Figure 8:
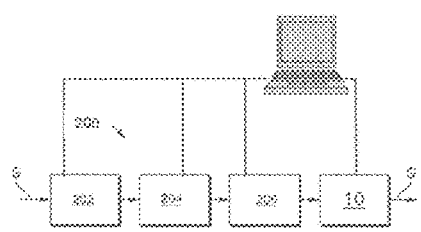
FIG. 8 is a schematic diagram of one embodiment of the disclosed in-line optical inspection system installed in a typical automotive glass forming and tempering line.
Figure 9:
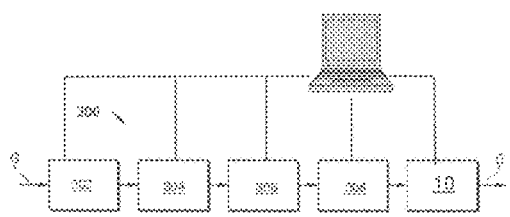
FIG. 9 is a schematic diagram of another embodiment of the disclosed in-line optical inspection system installed in a typical automotive windshield forming line.

The online optical inspection system 10 may, in turn, be incorporated into a system for fabricating glass sheets including one or more processing stations and one or more conveyors for conveying the glass sheets from station to station during processing, such as fabrication systems 200 and 300 schematically shown in FIGS. 8 and 9.

Referring now to FIGS. 1-4, the small defects apparatus 12 will be described in greater detail. In the disclosed embodiment, the first camera 24 may be a digital line scan camera. In one embodiment, for example, first camera 24 is a 12288 pixel X 1 pixel CCD line scan camera available as Basler Model Number 2000032201 from North Coast Technical Services. In the disclosed embodiment, the first camera is fitted with a Zeiss, 28 mm F-Mount, F/2-F22, Focal Range 0.24M—Infinity, Angular Field Diag/Horz/Vert 74°/65°/45° lens.

First background screen 20 is a lightbox that utilizes conventional lighting (such as LED or fluorescent lights) behind a translucent panel upon which the contrasting pattern is printed, painted, or otherwise applied using conventional methods. In the embodiment depicted in FIG. 4, the first pattern 22 consists of a series of alternating black and white bars (or stripes). In the depicted embodiment each bar is 0.75 mm wide, and the entire contrasting pattern 22 extends about 80 inches (i.e., of sufficient width to extend across an entire glass sheet part as it is conveyed on conveyors 16, 18), and is about 2 inches in dimension in the direction of conveyance. In this depicted embodiment first camera 22 may be activated with sufficient frequency to acquire approximately 2100 lines of data per image to thereby allow for construction of a relatively high resolution (e.g., 25 Mpixel) composite image of the glass as it is conveyed across the background screen 20. In this embodiment has been found that defects as small as about 8 mm can be identified.

The small defects apparatus 12 may also include light shield 34 interposed above the first background screen 20 in the path of the camera 24. Light shield 34 includes a slotted aperture 36 which allows the camera to acquire an image of the background pattern 22. Light shield 34 otherwise shields the surface of the glass sheet facing camera 24 as it is conveyed through the image acquisition zone to prevent camera 24 from detecting ambient light that might otherwise reflect off the surface of the glass.

Referring particularly to FIG. 3, the disclosed embodiment of the small defects apparatus 12 employs an upstream conveyor 16 and a downstream conveyor 18. In the disclosed embodiment each of upstream and downstream conveyors 16, 18 are belt-type conveyors. The discharge end of upstream conveyor 16 may be positioned adjacent to the charge end of conveyor 18 such that a gap 38 is defined between the adjacent conveyors 16, 18. Background screen 20 may be mounted below the plane of conveyance of the glass sheet such that the first pattern 22 is viewable by camera 24 (i.e., the light path, p, of the camera 24 extends through the glass sheet to the background screen 20) without any structural obstruction in the path between the camera 24 and the background screen 20. Thus, by employing adjacent conveyors with a suitable gap between the conveyors, an unobstructed image of the entire width of the glass sheet may be obtained. It should also be appreciated that various other types of conveyors (such as, for example, roller conveyors) may be employed in this embodiment without concern for structural obscuration in the glass sheet image data.

The first camera 24 is mounted to collect images of the first pattern 22 on background screen 20 transmitted through the glass sheet G retained as the glass sheet moves between the camera 24 and the background screen 20. The camera 24 is connected via a conventional data line to a computer 60 which may be suitably programmed to acquire the digital image data from the camera, process the image data to form a first set of image data for the selected area of interest from the multiple line scan images, obtain the desired resolution for the data, and analyze the data to identify as small marks/defects on/in the glass sheet according to the method of the present invention as described herein, and as further described in U.S. Patent Application Publication No. 2012/0098959 A1. The computer 60 may also be programmed to present the derived small defects information in both graphical (e.g., color-coded images) and statistical forms. If desired, various other statistical data which may be of interest can be derived and reported for selected area(s) of the glass sheet.

It should be appreciated that other cameras of various image acquisition speed and optical and electronic resolution may be employed depending upon the size and shape complexity of the glass parts and the conveyor speed, as well as the size and type of defects which are desired to be detected by the apparatus 12. The pattern 22 may similarly be modified in size and design depending upon desired operating and performance parameters. For example, in another embodiment, a series of alternating black and white bars, each of which is approximately 1 mm wide, are employed for pattern 22 with the disclosed camera to achieve satisfactory detection of defects of at least approximately 0.75 mm. These small defects include small marks or occlusions on/in the glass, such as roll marking, cloth marking, float defects, imprints, dirt within the laminate, and small vinyl distortion, many of which would generally not be detected, or "detected" but not recognized as small marks/occlusions on/in the glass, by conventional transmitted optical distortion measuring systems.

Referring now to FIGS. 1, 5 and 6, the transmitted optical distortion apparatus 14 will be described in greater detail. The second camera 32 is mounted to collect images of the second background screen 28 transmitted through the glass sheet mounted on the positioner 40. In the disclosed embodiment, the second camera 32 may be a commercially available CCD camera. In one embodiment, for example, second camera 32 is a 16 MPa, 3 frame-per-second GE 4900 Model CCD Camera available from Prosilica, Inc. of Burnaby, British Columbia, Canada, fitted with a Zeiss 50 mm F/s Makro-Planar T Manual Focus Lens, Part Number 17710845.

Second background screen 28 may be a lightbox that utilizes conventional lighting (such as LED or fluorescent lights) behind a translucent panel upon which the contrasting pattern is printed, painted, or otherwise applied using conventional methods. Pattern 30 on background screen 28 may provide a pattern of dark squares positioned on a light background at a known predetermined distance from each other, forming a rectangular grid such that the image of the grid is projected onto the camera 32 through the glass sheet, G, positioned therebetween. In the embodiment depicted in FIG. 5, the second pattern 30 consists of a uniform square dot array. Pattern 30 is sufficiently large that it provides a background for the entire glass sheet part when it is positioned by device 40.

It should be appreciated that other cameras of various image acquisition speed and optical and electronic resolution may be employed depending upon the size and shape complexity of the glass parts which are to be analyzed by apparatus 14. The second pattern 30 may similarly be modified depending upon desired operating and performance parameters.

Referring still to FIGS. 1 and 6, the transmitted optical distortion apparatus 14 may include a glass sheet acquisition and positioning device 40 which includes an exterior frame 42 mounted in proximity to the conveyor 18 between second background screen 28 and second camera 32. The glass sheet acquisition and positioning system 40 further includes a moveable glass sheet support frame 44 operably connected to exterior support frame 42 such glass sheet support frame 44 may be moved from a first, generally horizontal orientation to a second, upwardly-tilted orientation whereby glass sheet support frame 44 (and a glass sheet retained within the frame 44) is elevated from the plane of conveyor 18 to position the glass sheet between camera 32 and screen 38 at a preselected position (such as shown in FIG. 6), so that the transmitted optical distortion apparatus 14 may collect the desired data for that particular glass sheet.

The moveable glass sheet support frame 44 may thereafter be returned to its generally horizontal position (as shown in FIG. 1) and release the glass sheet from the frame 44 back onto the conveyor 18 for conveyance of the glass sheet for further processing by the glass sheet processing system. The glass sheet acquisition and positioning device 40 further includes a programmable control (such as computer 26) including at one or more processors programmed to execute logic for controlling the device 40 to perform the acquisition and positioning functions described herein.

In one embodiment, acquisition and positioning device 40 may be of the type described in U.S. Patent Application Publication No. 2016/0257598 A1, the disclosure of which Publication is hereby incorporated herein in its entirety. However, other embodiments of acquisition and positioning device 40 may be employed in system 10 to appropriately position each glass sheet for conducting the transmitted optical distortion for each glass sheet at the desired viewing angle.

The second camera 32 is mounted to collect images of the pattern 30 on second background screen 28 transmitted through the glass sheet G retained on the glass sheet acquisition and positioning device 40. The camera 32 is connected via a conventional data line to a computer 60 which may be suitably programmed to acquire the digital image data from the camera, process the second set of image data to obtain the desired resolution for the data, and analyze the data to develop various indicia of transmitted optical distortion in the glass sheet according to the method of the present invention as described herein, and as further described in U.S. Patent Application Publication No. 2012/0098959 A1. The computer 60 may also be programmed to present the derived image distortion information in both graphical (e.g., color-coded images) and statistical forms. If desired, various other statistical data can be derived and reported for pre-defined areas of the glass sheet, including the maximum, minimum, range, mean, and standard deviation in lens power, or other indices of distortion which may be of interest.

The glass sheet optical characteristics inspection system 10 may also include a glass sheet part identifier including a shape sensor, such as first camera 24, mounted in proximity to the conveyor 16, upstream from the transmitted optical distortion apparatus 14. The sensor may be controlled for activation to acquire data associated with the shape of a glass sheet traveling on the conveyor. The sensor may be operably connected to one or more processors, such as computer 60 (as shown in FIG. 1), wherein the computer includes logic for analyzing the data acquired by the sensor and identifying the glass sheet as one of a set of known part shapes stored in memory in the computer 60.

In the illustrated embodiment of the system 10, the part identifier also includes a background screen mounted below the conveyor to provide a suitably contrasting background so that the sensor can acquire data suitable to allow the system logic to efficiently discern the shape of the glass part as it is conveyed between the sensor and the background screen. In the illustrated embodiment, part identifier 22 employs first camera 24 as the sensor and first background screen 20 as its background screen. In this disclosed embodiment, the first set of image data acquired by the first camera may be utilized for both the small defects detection performed by apparatus 12 and the part identification described herein.

It will be appreciated that, in the disclosed embodiment, identification of the part type allows acquisition and positioning device 40 to retain and position, respectively, the glass sheet so that each of the identified parts is positioned such that the centerline of the glass sheet is coincident with the principal axis of camera 32 for image acquisition by the optical distortion apparatus 14. It will also be appreciated that the device 40 system may be programmed to position a glass sheet to any desired angle based upon part type, and/or user preference.

It should also be appreciated that the part identifier may be used to detect the boundary of a glass sheet and set the first selected area (i.e., the area of interest to be analyzed) for that sheet for utilization by the small defects apparatus 12.

In one embodiment, the inspection system 10 may be of the type described in U.S. Patent Application Publication No. 2012/0098959 A1, the disclosure of which Publication is hereby incorporated herein in its entirety.

The system 10 may be programmed by the user to graphically and numerically display various indicia of optical distortion detected by apparatus 14, including those indicia most relevant to industry standards such as ECE R43, or other indicia considered relevant in the industry to the analysis of the optical transmission quality of formed and fabricated glass sheets. The system 10 may, as well, be programmed to display the locations of small defects identified by apparatus 12.

Figure 7:
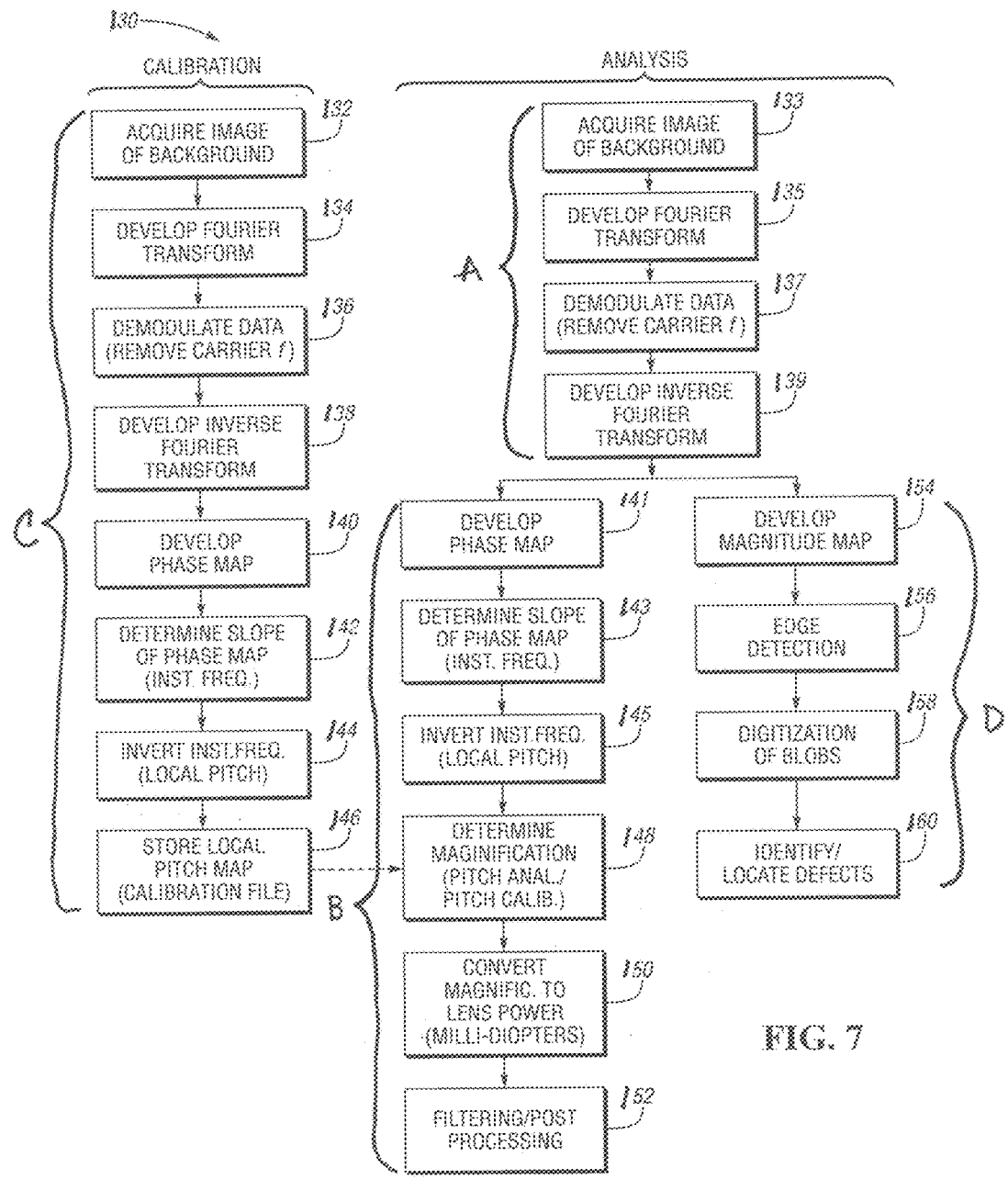
FIG. 7 is a flow chart of one of the disclosed process operations performed as part of the small defects and transmitted optical distortion analyses.

FIG. 7 illustrates the principle image distortion and small defects analysis process 130 that may be employed for each glass sheet by the system 10. In particular, the transmitted optical distortion apparatus 14 may employ each of steps 133-152 (collectively identified in groups A, B and D in FIG. 7) on the second set of image data acquired for each glass sheet.

According to the disclosed method 130, the system is first calibrated at even-numbered steps 132-146 (collectively designated as set C). Calibration begins, at 132, by acquiring an image of the background using a CCD camera without a test piece of glass mounted between the camera and the background. At 134, a Fourier transform of the acquired calibration image data is developed. The resulting data is modulated by the fundamental frequency of the grid pattern on the screen in both the horizontal and vertical directions. The bandwidth is narrowed to eliminate unwanted signal data such as second harmonics. At 136 the transformed data is demodulated, to remove the carrier frequency. An inverse Fourier transform of the demodulated data is then developed, at 138, with the resulting data yielding a two-dimensional complex number associated with each pixel having a phase component and a magnitude component. A phase map of the inverse Fourier transform is then developed, at 140, by computing the inverse tangent of the imaginary portion of the two-dimensional complex number divided by the real portion of the two-dimensional complex number for each pixel in the image.

The slope of the phase map is representative of the instantaneous frequency at each pixel in the image. These values are developed at 142. At 144, the instantaneous frequency at each pixel is inverted to obtain the local pitch. This local pitch map is then stored, at 146, as the calibration file. This calibration file is then used by the optical distortion apparatus 14 in the analysis of the phase portion of the images acquired for each glass sheet subsequently tested using the system.

The analysis performed by optical distortion apparatus 14 for each glass sheet is illustrated at odd-numbered steps 133-145 and 148-150 (collectively designated as sets A and B) in FIG. 7. Once the piece is positioned for analysis, the initial steps, indicated at 133-145, are identical to steps 132-144 described above, except that an image of the second background screen 28 is acquired, at 133, using a CCD camera with the subject glass part (the "test part") positioned between the camera 32 and the background screen 28. The resolved image data is then processed as further described below to develop the optical distortion indicia for each glass sheet. The optical distortion indicia for the glass test part is developed as shown in the steps designated as set B of FIG. 7. Once the local pitch as determined for in the test part image, at 145, the system, at 148, determines the magnification at each pixel by dividing the local pitch of the test part image by the local pitch of the calibration image at each respective pixel. These pixel-by-pixel values are then utilized, at 150, to develop a lens power (focal length) value for each pixel in the image of the test part. The lens power is typically expressed in millidiopters, the quantity often used in the glass industry for this measurement. The system proceeds in a stepwise fashion to determine magnification and lens power values for each of the dots in the image. The lens power may then also be resolved into its vertical and horizontal components.

Referring again to FIG. 7, the digital image data acquired from the camera is resolved, or filtered, at a post-processing step 152, to eliminate noise, reduce resolution of the image to that approximating how the image would be perceived by a human viewer, and/or otherwise reduce the amount of image data as desired to eliminate unnecessary processing time. Various known filtering techniques, such as data averaging, may be employed to resolve the data. In one embodiment, two standard filters are developed to provide data which has been empirically shown to correlate with the "4-5-6" and "4-5-12" filters used on another optical distortion measuring system currently available from ISRA Surface Vision GmbH, so as to allow industry users to develop comparable distortion indicia for their products regardless of which measuring system is used. The bandwidth is narrowed to eliminate unwanted signal data such as second harmonics.

The analysis that may be performed by small defect detection apparatus 12 for each glass sheet is illustrated at odd-numbered steps 133-139 and steps 154-160 (collectively identified in sets A and D in FIG. 7) on the first set of image data acquired for each glass sheet. The inverse Fourier transform of the magnitude (intensity) component of the complex number, developed at 139 (as described above in connection with step 138), is further developed, at 154, to yield data corresponding to an intensity map of the image. This is accomplished by determining the square root of the sum of the squares of the imaginary portion of the two-dimensional complex number and the real portion of the two-dimensional complex number for each pixel in the image. This intensity (or magnitude) map is similar to a gray-scale image of the glass sheet illuminated by a point source of light, including intensity discontinuities correspond to small BLOBs (binary large objects), corresponding to optical or obstructive defects on the glass sheet. This intensity map is analyzed, at 156, using conventional edge detection algorithms to locate the edges of the BLOBs. One type of edge detection algorithm that may be used for this purpose is the Canny algorithm.

In the disclosed embodiment, the defect detection apparatus 12 utilizes image processing techniques and software available from Matrox Electronic Systems, Ltd. to perform the part identifier and BLOB detection functions. Of course, other commercially available techniques and/or software may be employed for these purposes.

Once the edges of the BLOBs are detected, all BLOBs satisfy a predefined size threshold are then digitized, at 58, to identify the centers of these selected BLOBs. The typical "small defects" desired to be identified corresponds to BLOBs ranging in diameter from about 10 to about 300 pixels (i.e., 1-5). The predefined defect size may be specified by the system user. For example, one defect size range has been set to 10-200 pixels. Each of the small defects satisfying the predefined criteria are located at 160. The location of each of these small visible surface defects may then be displayed on the vertical and horizontal distortion images displayed by the system. Surface defects/spots as small as about 0.8 mm may be detected using this analysis in the dislosed apparatus 12.

Thus, both the optical distortion characteristics and other small optical/obstruction defects can be developed and identified for a particular glass sheet by isolating and analyzing, respectively, the phase and magnitude components of the inverse Fourier transform of the data acquired from a single digital image of the sheet.

FIG. 8 illustrates a typical glass sheet heating, bending, and tempering system 200 which includes the in-line optical inspection system 10 of the present invention. In this installation, the glass sheets (indicated as G) enter a heating zone 202 where the glass is softened to a temperature suitable for forming the glass into the desired shape. The heated glass sheet is then conveyed to a bending station 204 where the softened sheet is formed to the desired shape, and thereafter further conveyed to a cooling station 206 where the glass sheet is cooled in a controlled manner to achieve the appropriate physical characteristics. In this embodiment, the glass sheet would then be conveyed out of the cooling station onto a conveyor from which the sheet is conveyed and positioned for image acquisition and analysis by both the small defect detection apparatus 12 and the transmitted optical distortion apparatus 14 of the optical inspection system 10 according to the present invention.

FIG. 9 similarly schematically illustrates an in-line optical inspection system 10 of the present invention in a typical automotive windshield fabrication system 300, which may include a heating station 302, a bending station 304, a cooling station 306, and a lamination station 308, upstream of the optical inspection system 10.

Figure 10:
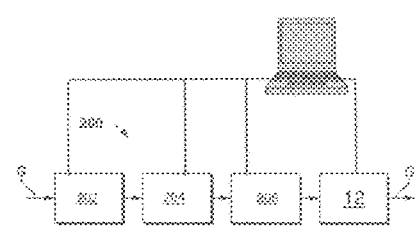
FIG. 10 is a schematic diagram of one embodiment of the disclosed apparatus for measuring small defects installed online in a typical automotive glass forming and tempering line.

FIG. 10 illustrates a typical glass sheet heating, bending, and tempering system 200 which includes the disclosed small defect detection apparatus 12. In this installation, the glass sheets (indicated as G) enter a heating zone 202 where the glass is softened to a temperature suitable for forming the glass into the desired shape. The heated glass sheet is then conveyed to a bending station 204 where the softened sheet is formed to the desired shape, and thereafter further conveyed to a cooling station 206 where the glass sheet is cooled in a controlled manner to achieve the appropriate physical characteristics. In this embodiment, the glass sheet would then be conveyed out of the cooling station onto a conveyor from which the sheet is conveyed and positioned for image acquisition and analysis by apparatus 12 according to the present invention.

Figure 11:
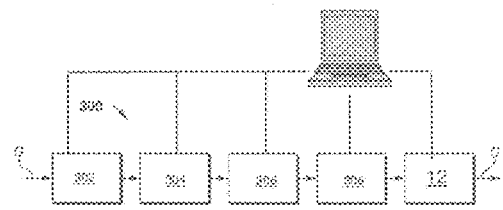
FIG. 11 is a schematic diagram of one embodiment of the disclosed apparatus for measuring small defects installed online in a typical automotive windshield forming line.

FIG. 11 similarly schematically illustrates the disclosed small defect detection apparatus 12 in a typical automotive windshield fabrication system 300, which may include a heating station 302, a bending station 304, a cooling station 306, and a lamination station 308, upstream of the apparatus 12.

It will be appreciated that the transport and conveyance of the glass can be achieved by using known techniques such as by roller, air-float, or belt conveyors, positioners, and robotic arms, in order to handle the glass in the manner described. It will also be appreciated that a plurality of conveyors, each of which may be independently controlled to move the glass sheets through the different processing stations at speeds to efficiently govern the flow and processing of the glass sheets throughout systems 200, 300.

Selected data output by the disclosed in-line optical inspection system 10 may also be provided as input to the control logic for the associated glass sheet heating, bending, and tempering system 200 (or automotive windshield fabrication system 300) to allow the control(s) for one or more of the stations the glass sheet system to modify its(their) operating parameters as a function of the optical data developed from previously processed glass sheets.

It will be appreciated that the optical inspection system 10 and/or the small defect detection apparatus 12 of the present invention could alternatively be mounted in-line at various other points in the above-described and other glass sheet fabrication systems as desired to maximize the production rate of the system, so long as the small defect identification and/or optical distortion measurements are taken after the glass sheet has been formed to its final shape.

It will also be appreciated by those skilled in the art that, although the cameras 24, 32 and background screens 20, 28 are arranged in the illustrated embodiments such that the path between each of the cameras 24, 32 and their corresponding background screens 20, 28 is generally parallel to the direction of conveyance of the glass, various alternative arrangements of the system 10 along conveyor(s) suitably connected to the glass sheet processing system may be employed without departing from the spirit of the invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An inline apparatus for measuring small optical or obstructive defects in a selected area of a glass sheet, the inline apparatus installed in a system for fabricating glass sheets including one or more processing stations and one or more conveyors for conveying the glass sheet from station to station during processing, the inline apparatus comprising:
   an upstream conveyor and a downstream conveyor, each of which convey each glass sheet in a generally horizontal orientation, wherein the upstream conveyor and downstream conveyor are positioned end-to-end with their adjacent ends spaced apart by a selected size gap such that, as a glass sheet is conveyed from the upstream conveyor to the downstream conveyor, a portion of the glass sheet is unsupported over the gap;
   a background screen including contrasting elements arranged in a pre-defined pattern, wherein the background screen extends across the full dimension of the selected area in the direction transverse to the direction of conveyance;
   a line scan camera for acquiring a set of image data comprising multiple images of the background screen, each image associated with a portion of the selected area of the glass sheet, as the glass sheet is conveyed across the path between the camera and the background screen, the background screen mounted such that the camera may acquire multiple images of the background screen as the unsupported portion of the glass sheet is conveyed therebetween; and
   a computer including at least one processor programmed to execute logic for receiving the set of image data, developing an intensity map from the set of image data, and identifying and locating the small defects from the intensity map.

2. The apparatus of claim 1 further including a glass sheet part identifier including a sensor for acquiring data associated with the shape of a glass sheet travelling on a conveyor upstream from the inline apparatus, wherein the at least one processor includes logic for analyzing the acquired data and identifying the glass sheet as one of a set of known part shapes, and wherein the selected area of the glass sheet is defined based in part upon the identified part shape.

3. The apparatus of claim 2 wherein the sensor is the line scan camera and the acquired data is the set of image data.

4. The apparatus of claim 1 further including a glass sheet part identifier including a sensor for acquiring data associated with the shape of a glass sheet travelling on a conveyor upstream from the inline apparatus, wherein the at least one processor includes logic for analyzing the acquired data and identifying the shape of the glass sheet, and wherein the selected area of the glass sheet is defined based in part upon the identified shape.

5. The apparatus of claim 4 wherein the sensor is the camera and the acquired data is the set of image data.

6. The apparatus of claim 1 wherein the logic for developing an intensity map from the set of image data includes logic for developing a Fourier transform of the image data, de-modulating the Fourier transform, developing an inverse Fourier transform of the de-modulated data, yielding a two-dimensional complex number associated with each pixel, said complex number having a phase component and a magnitude component, and developing an intensity to map of the inverse Fourier transform by determining the square root of the sum of the squares of the imaginary portion of the two-dimensional complex number and the real portion of the two-dimensional complex number for each point of interest in the image.

7. The apparatus of claim 1 wherein the small optical or obstructive defects are identified and located for each point of interest in the image by analyzing the intensity map to locate the edges of small blobs.

8. An online apparatus for measuring small optical or obstructive defects in a selected area of a glass sheet in a system for fabricating glass sheets including a heating station for heating the glass sheet to a temperature adequate to soften the glass for forming into a desired shape, a bending station wherein the softened sheet is formed to the desired shape, a cooling station wherein the formed glass sheet is cooled in a controlled manner, and one or more conveyors for conveying the glass sheet from station to station during processing, the apparatus including:
   an upstream conveyor and a downstream conveyor, each of which convey each glass sheet in a generally horizontal orientation, wherein the upstream conveyor and downstream conveyor are positioned end-to-end with their adjacent ends spaced apart by a selected size gap such that, as a glass sheet is conveyed from the upstream conveyor to the downstream conveyor, a portion of the glass sheet is unsupported over the gap;
   a background screen including contrasting elements arranged in a pre-defined pattern, wherein the background screen extends across the full dimension of the selected area in the direction transverse to the direction of conveyance;
   a line scan camera for acquiring a set of image data comprising multiple images of the background screen, each image associated with a portion of the selected area of the glass sheet, as the glass sheet is conveyed across the path between the camera and the background screen, the background screen mounted such that the camera may acquire multiple images of the background screen as the unsupported portion of the glass sheet is conveyed therebetween; and
   a computer including at least one processor programmed to execute logic for receiving the set of image data, developing an intensity map from the set of image data, and identifying and locating the small defects from the intensity map.

9. The apparatus of claim 8 further including a glass sheet part identifier including a sensor for acquiring data associated with the shape of a glass sheet travelling on a conveyor upstream from a second background screen and a computer including at least one processor programmed to execute logic for analyzing the acquired data and identifying the glass sheet as one of a set of known part shapes.

10. A method for measuring small defects in a selected area of a glass sheet as the glass sheet is conveyed in a system for fabricating glass sheets including one or more processing stations and one or more conveyors for conveying the glass sheet from station to station during processing, the method including at least the steps of:

providing an upstream conveyor and a downstream conveyor, each of which convey each glass sheet in a generally horizontal orientation, wherein the upstream conveyor and downstream conveyor are positioned end-to-end with their adjacent ends spaced apart by a selected size gap such that, as a glass sheet is conveyed from the upstream conveyor to the downstream conveyor, a portion of the glass sheet is unsupported over the gap;

providing a background screen including contrasting elements arranged in a pre-defined pattern, wherein the background screen extends across the full dimension of the selected area in the direction transverse to the direction of conveyance of the glass sheet, and wherein the background screen is mounted such that a line scan camera may acquire multiple images of the background screen as the unsupported portion of the glass sheet is conveyed therebetween;

conveying the glass sheet across the path between the line scan camera and the background screen;

acquiring from the line scan camera a set of image data comprising multiple images of the background screen, each image associated with a portion of the selected area of the glass sheet, as the glass sheet is conveyed across the path between the camera and the background screen; and executing logic on a computer including at least one processor for receiving the set of image data, developing an intensity map from the set of image data, and identifying and locating the small defects from the intensity map.

\* \* \* \* \*